United States Patent
Mayrand

(10) Patent No.: US 12,156,829 B2
(45) Date of Patent: Dec. 3, 2024

(54) REUSABLE PENILE ATTACHMENT FOR URINARY INCONTINENCE WHICH USES PRESSURE DIFFERENTIAL AS MEANS OF ATTACHMENT

(71) Applicant: Gerald Mayrand, St-Hubert (CA)

(72) Inventor: Gerald Mayrand, St-Hubert (CA)

( * ) Notice: Subject to any disclaimer, the term of this patent is extended or adjusted under 35 U.S.C. 154(b) by 850 days.

(21) Appl. No.: 17/223,908

(22) Filed: Apr. 6, 2021

(65) Prior Publication Data

US 2021/0220163 A1 Jul. 22, 2021

Related U.S. Application Data

(63) Continuation-in-part of application No. 16/254,594, filed on Jan. 23, 2019, now abandoned.

(51) Int. Cl.
*A61F 5/453* (2006.01)
*A61F 5/44* (2006.01)

(52) U.S. Cl.
CPC ............ *A61F 5/453* (2013.01); *A61F 5/4408* (2013.01)

(58) Field of Classification Search
CPC ................................ A61F 5/453; A61F 5/4408
See application file for complete search history.

(56) References Cited

U.S. PATENT DOCUMENTS

| | | |
|---|---|---|
| 3,742,953 A | 7/1973 | Lee |
| 4,475,909 A | 10/1984 | Eisemberg |
| 4,626,250 A | 12/1986 | Schneider |
| 4,656,675 A | 4/1987 | Fajnsztajn |
| 5,084,037 A | 1/1992 | Barnett |
| 5,334,175 A | 8/1994 | Conway et al. |
| 5,423,785 A | 6/1995 | Hart |
| 5,630,429 A | 5/1997 | Dann |
| 5,685,870 A | 11/1997 | Tanghoj |
| 5,752,944 A | 5/1998 | Dann |
| 5,840,058 A * | 11/1998 | Ammann ............... A61M 5/365 604/131 |
| 5,897,540 A | 4/1999 | Grundke et al. |
| 2005/0076917 A1* | 4/2005 | Wray ........................ A61F 6/04 428/407 |
| 2020/0390591 A1* | 12/2020 | Glithero .................. A61F 5/451 |

\* cited by examiner

*Primary Examiner* — Steven O Douglas

(57) ABSTRACT

A reusable penile attachment for urinary incontinence which uses pressure differential as means of attachment, a cup having a depth having an opening having a first width and an exit having a second width, wherein the first width is greater than the second width; and, wherein the opening of the cup is configured to fit onto a glans of a penis. The exit is fluidly connected to a connector which includes an integrated square angle elbow which positions the connector into a generally horizontal configuration. The connector then connects to a tube having a first end and a second end, wherein the first end is attached to the connector; a collection bag having attachment straps, wherein the collection bag is attached to the second end of the tube; the collection bag is configured to collect urine leakage. The horizontal configuration in cooperation with the clothes worn by the intended user provides a pressure differential for retaining the cup onto the penis and for retaining is a suction effect created by the shape of the cup.

5 Claims, 4 Drawing Sheets

FIG. 3A      FIG. 3B
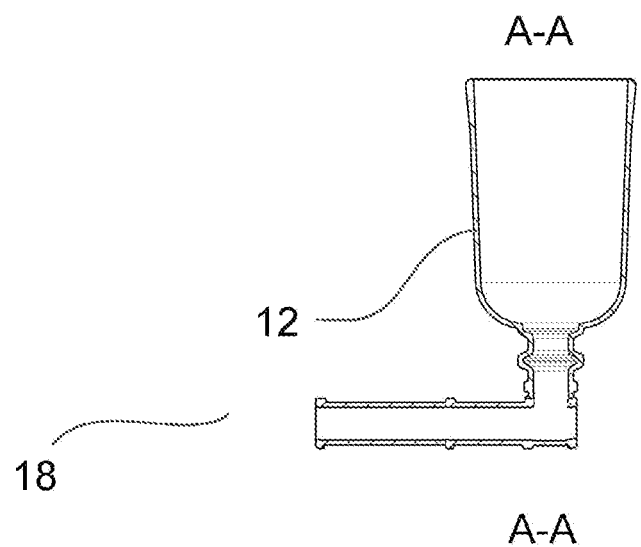
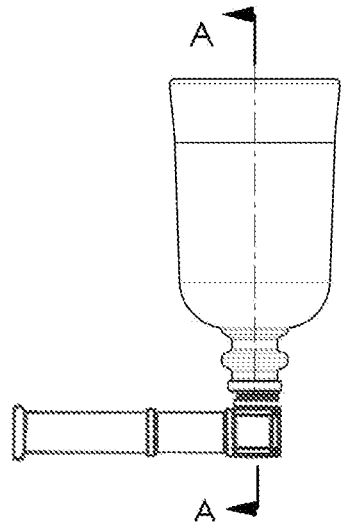
FIG. 4A      FIG. 4B
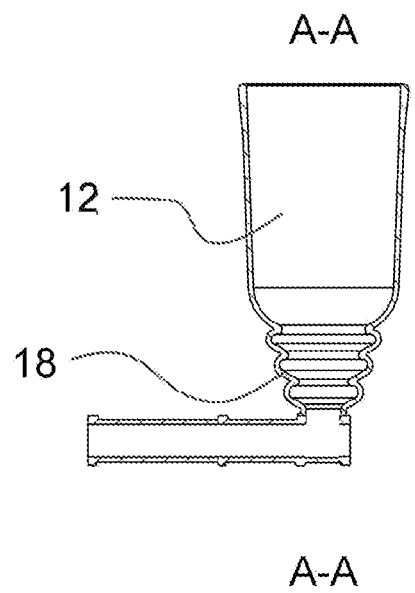
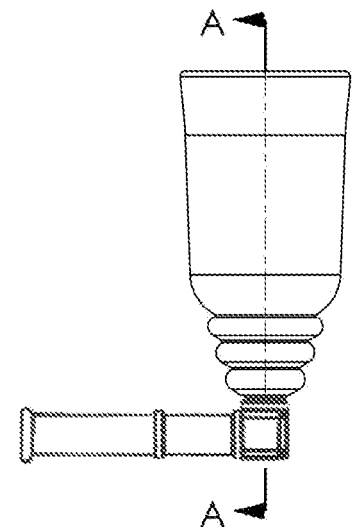

REUSABLE PENILE ATTACHMENT FOR URINARY INCONTINENCE WHICH USES PRESSURE DIFFERENTIAL AS MEANS OF ATTACHMENT

CROSS-REFERENCE TO RELATED APPLICATIONS

The present application claims priority to U.S. patent application No. 20190224038 filed 07è25è2019 which was based on United Kingdom Patent Application serial number GB1801184.1, filed on Jan. 24, 2018 entitled "An improved and reusable penile attachment", the disclosure of which is hereby incorporated in its entirety at least by reference.

BACKGROUND OF THE INVENTION

1. Field of the Invention

The present invention relates generally to a penile sheath or attachment for incontinence but more particularly to a reusable penile attachment using pressure differential as means of attachment

2. Description of Related Art

Urinary incontinence (UI), also known as involuntary urination, is any uncontrolled leakage of urine. Incontinence among men is a growing problem worldwide and has been identified as an important issue in geriatric health care.

In order to improve the quality of life in men suffering from incontinence, there exist several solutions ranging from penile clamps for simple dripping to sheaths connected to a bag for more serious cases of incontinence. In cases where a sheath or penile attachment is connected via a tube to a bag, the penile attachment is to be changed every 24 hours to a maximum of 48 hours in some devices. The methods of affixing the attachment to the penis include, glue, straps, clamps etc., which are all uncomfortable. Additionally, it can take time fitting and removing the device and requires the pubic area to be shaved for some attachments. Furthermore, these attachments are prone to slipping off and unsuitable for sporting and other activities which require movement. Also, they can be quite uncomfortable when partially immobile in a wheelchair.

There hence exists a need for improvement in penile attachments for incontinence which can be quick to install, suitable for a variety of movements and reusable, thereby enhancing the quality of life for men of all ages suffering from incontinence.

BRIEF SUMMARY OF THE INVENTION

In one aspect of the reusable penile attachment for urinary incontinence which uses pressure differential as means of attachment, a cup having a depth comprising an opening having a first width and an exit having a second width, wherein the first width is greater than the second width; and, wherein the opening of the cup is configured to fit onto a glans of a penis. Cups come in different sizes to adapt to different penis sizes. The exit is fluidly connected to a connector which is comprised of an integrated square angle elbow which positions the connector into a generally horizontal configuration. The connector then connects to a tube having a first end and a second end, wherein the first end is attached to the connector; a collection bag having attachment straps, wherein the collection bag is attached to the second end of the tube; the collection bag is configured to collect urine leakage. The horizontal configuration in cooperation with the clothes worn by the intended user provides a first means for retaining the cup onto the penis the second means for retaining is a suction effect created by the shape of the cup and the lubricant. Also, the horizontal configuration makes it possible to wear shorts as the collection bag can be attached higher up on the thigh so as to be hidden.

In one embodiment, the attachment straps are configured to attach to a leg. In one embodiment, the reusable penile attachment using pressure differential as means of attachment may be washed and reused.

In yet another embodiment, the user wears a pair of boxer short having an interior pocket configured and sized to hold the collection bag.

In another aspect of the invention, a method to collect urinary leakage of a user is provided, comprising the steps of: a) assembling the cup to the connector and the connector to the tube; b) putting a lubricant inside the cup or on his penis (or both); c) pressing on the collection bag so as to remove the air therein and connecting one of the end of the tube to the collection bag; d) inserting the cup until the exit touches the tip of the glans; e) gently pulling on the cup so as to create a pressure differential in the area between the exit of the cup and the tip of the glans and the ambient pressure outside the cup.

BRIEF DESCRIPTION OF THE SEVERAL VIEWS OF THE DRAWINGS

Other features and advantages of the present invention will become apparent when the following detailed description is read in conjunction with the accompanying drawings, in which:

FIG. 3A is a cutaway view of a first penile attachment taken along A-A of FIG. 3B.

FIG. 3B is a side view of the first penile attachment according to an embodiment of the present invention.

FIG. 4A is a cutaway view of a second penile attachment taken along A-A of FIG. 4B.

FIG. 4B is a side view of the second penile attachment according to an embodiment of the present invention.

DETAILED DESCRIPTION OF THE PREFERRED EMBODIMENT

The following description is provided to enable any person skilled in the art to make and use the invention and sets forth the best modes contemplated by the inventor of carrying out their invention. Various modifications, however, will remain readily apparent to those skilled in the art, since the general principles of the present invention have been defined herein to specifically provide an improved and reusable penile attachment.

Figure 1:
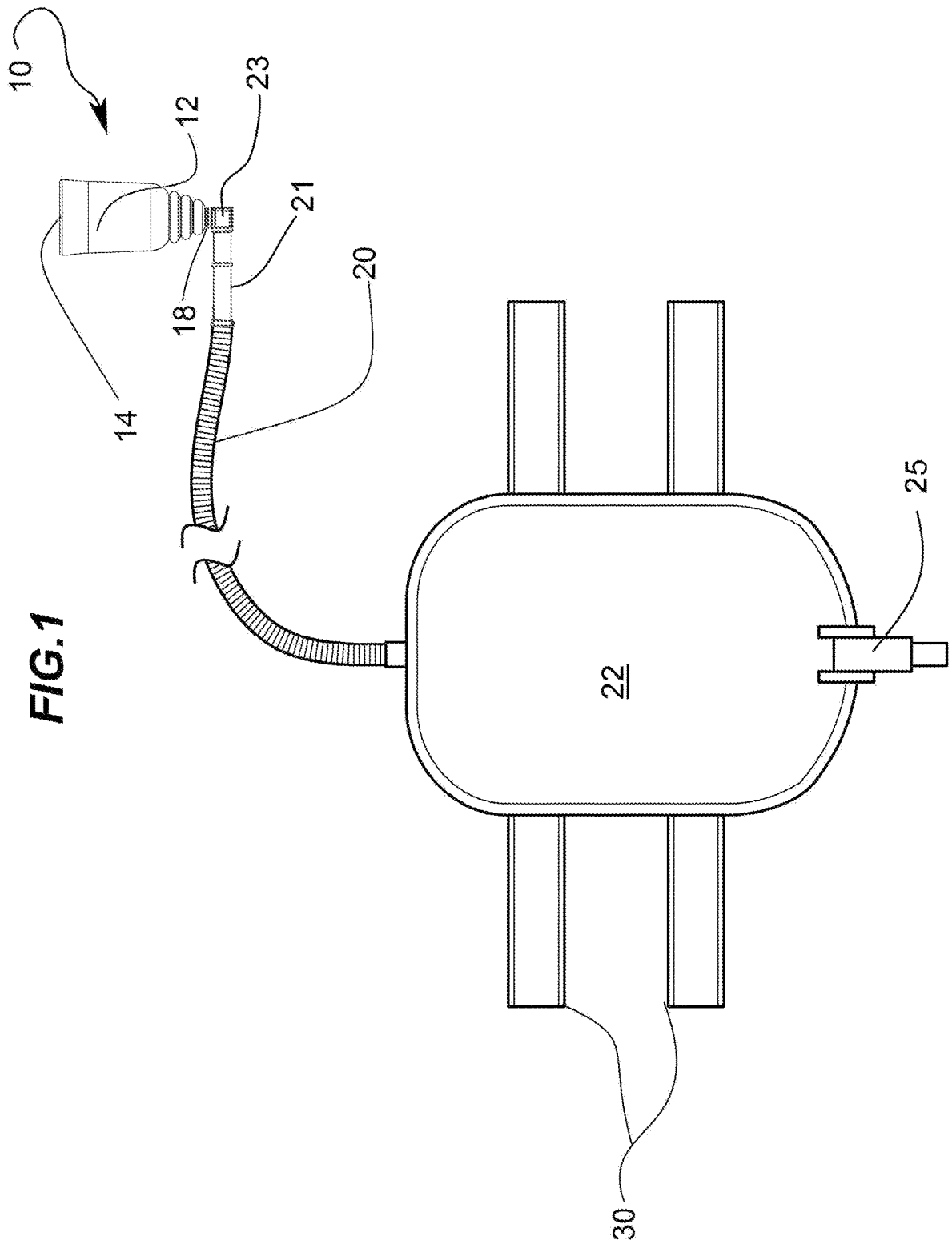
FIG. 1 is a front view of an improved and reusable penile attachment showing the collection bag and tubing according to an embodiment of the present invention.

Referring now to FIG. 1, a reusable penile attachment for urinary incontinence which uses pressure differential as means of attachment 10 is illustrated. The penile attachment comprises a cup 12 having a wide opening 14 and a narrow exit 18. In one embodiment, the narrow exit is fluidly connected to a connector 21 which is comprised of an integrated square angle elbow 23 which positions the connector into a generally horizontal configuration. The connector then connects to a tube 20 which connects to a collection bag 22. The collection bag includes attachment straps 30 for attaching the collection bag to the user. This will be described in greater detail below. The collection bag has a drain plug 25 to drain its content, as is known in the art.

The horizontal configuration of the connector is kept in place by the combination of the lubricant inside the cup and the clothes of the intended user—whether pants, loose shorts or tight shorts—, which help in keeping the cup on the glans which, along with a suction effect created by the shape of the cup and the lubricant, provides the necessary means for holding the cup onto the penis without the need of any other means of attachment.

Figure 2:
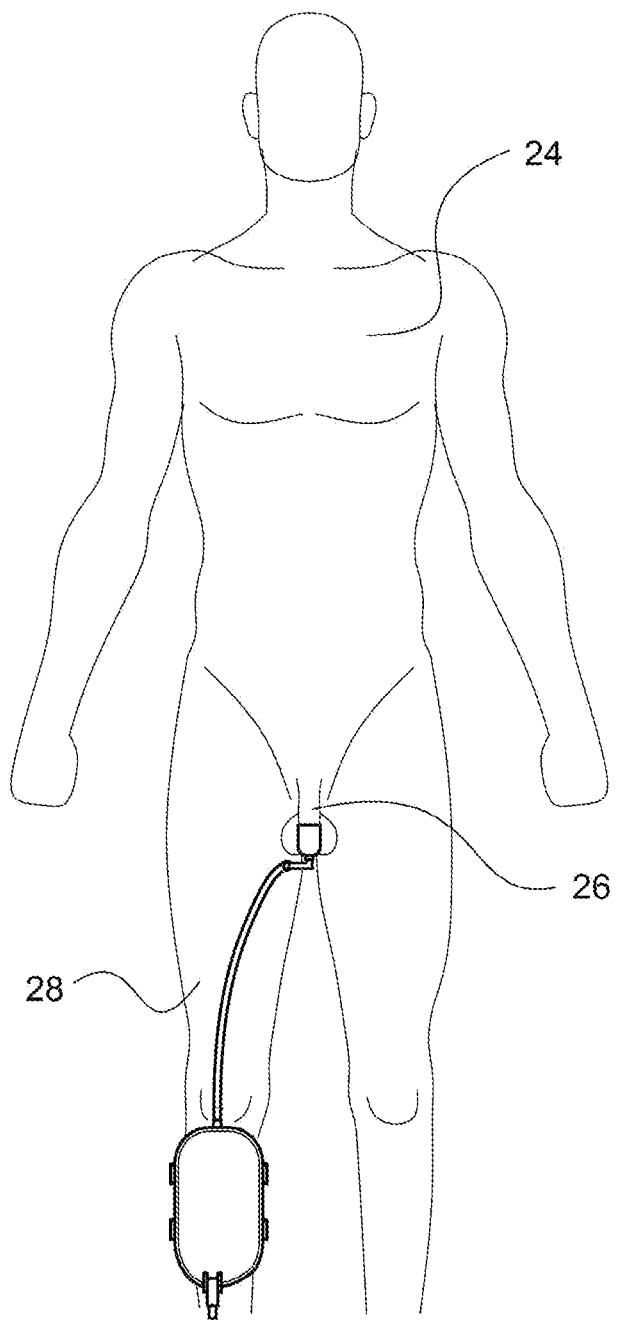
FIG. 2 illustrates the improved and reusable penile attachment in use according to an embodiment of the present invention.
Figure 5:
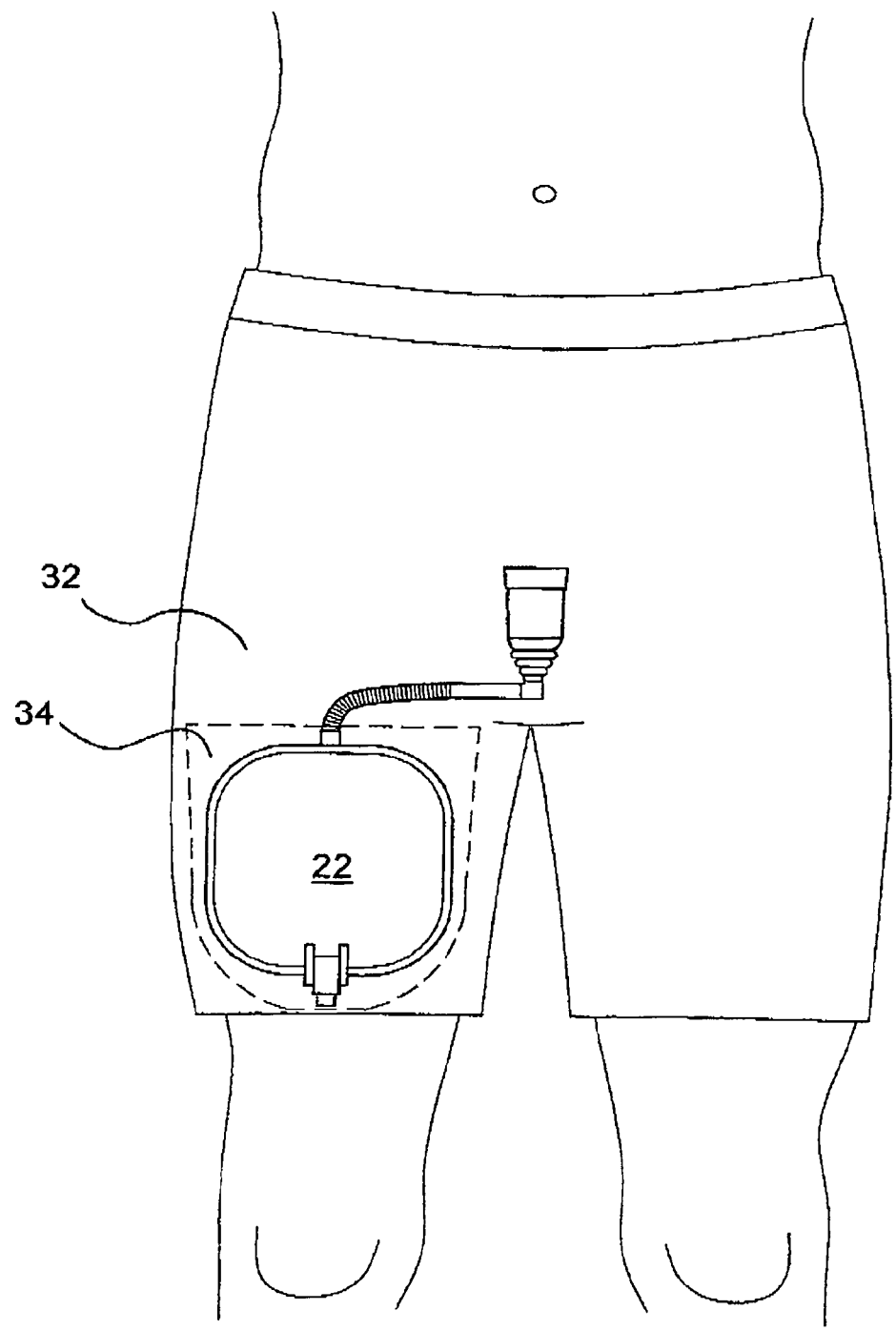
FIG. 5 is a front view of a user wearing a pair of specially designed boxer shorts having an interior pocket configured and sized for receiving the collection bag.

Referring now to FIG. 2, the improved and reusable penile attachment is in use. During use, opening 14 is configured to fit onto a glans 16 of a penis 26 of a user 24. The collection bag 22 is then attached to a suitable portion of the user's leg 28. It should be understood, that the location of the collection bag may vary. In one embodiment, the straps have hook and loop fasteners, or other suitable attachment means known in the art to affix the straps to each other. Similarly, the reverse is done when the user detaches the device. In one embodiment, a lubricant (not shown) is used when affixing the cup on the glans of the penis. Advantageously, the penile attachment remains affixed until it is physically pulled off or detached without the use of glue. After detachment, the penile attachment may be washed and reused.

Referring now to FIGS. 3A-B and 4A-B, show a first and second penile attachment design respectively. As illustrated, both designs have similar cup 12 designs however they each have different narrow exit 18 designs. The second penile attachment shown in FIGS. 4A-B has a bellows style exit 18' which starts with a wide diameter which becomes narrower as it connects to the connector. The first penile attachment shown in FIGS. 3A-B is shorter, has a diameter at the exit 18 generally equivalent to the diameter as it connects with the connector. It should be understood, that the two designs are just exemplary embodiments, and other designs are possible while remaining within the scope of this invention.

Furthermore, when a user intends to wear bermuda shorts, for example, he can put on a custom pair of specially designed boxer shorts 32 which have a pocket located on the interior side of the boxer short 32 which is configured and sized for putting in the collection bag 22. Of course, the specially designed boxer shorts can also be worn under pants. This avoids having to have the collection bag strapped around one's thigh.

The intended user can use the invention by following the steps of:
a) assembling the cup to the connector and the connector to the tube;
b) putting a lubricant inside the cup or on his penis (or both);
c) pressing on the collection bag so as to remove the air therein and connecting one of the end of the tube to the collection bag;
d) inserting the cup until the exit touches the tip of the glans;
e) gently pulling on the cup so as to create a pressure differential in the area between the exit and the tip of the glans and the ambient pressure outside the cup.

Although the invention has been described in considerable detail in language specific to structural features and or method acts, it is to be understood that the invention defined in the appended claims is not necessarily limited to the specific features or acts described. Rather, the specific features and acts are disclosed as exemplary preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. Such variations and alternate embodiments are contemplated, and can be made without departing from the spirit and scope of the invention.

It should further be noted that throughout the entire disclosure, the labels such as left, right, front, back, top, bottom, forward, reverse, clockwise, counter clockwise, up, down, or other similar terms such as upper, lower, aft, fore, vertical, horizontal, oblique, proximal, distal, parallel, perpendicular, transverse, longitudinal, etc. have been used for convenience purposes only and are not intended to imply any particular fixed direction or orientation. Instead, they are used to reflect relative locations and/or directions/orientations between various portions of an object.

In addition, reference to "first," "second," "third," and etc. members throughout the disclosure (and in particular, claims) are not used to show a serial or numerical limitation but instead are used to distinguish or identify the various members of the group.

What is claimed is:

1. A reusable penile attachment for urinary incontinence using pressure differential as means of attachment comprising:
a cup having a depth comprising an opening having a first width having a first shape and an exit having a second width having a second shape, wherein the first width is greater than the second width, wherein the first shape and the second shape are made in different sizes in order to align with a user's penis girth, resulting in an airtight fit for the purpose of implementing a pressure differential attachment means;
the exit is fluidly connected to a connector which is comprised of an integrated square angle elbow which positions the connector into a generally horizontal configuration; the connector then connects to a tube having a first end and a second end, wherein the first end is attached to the exit;
a collection bag having attachment straps, wherein the collection bag is attached to the second end of the tube; and,
wherein the opening of the cup is configured to fit onto a glans of a penis, and the collection bag is configured to collect urine leakage.

2. The reusable penile attachment of claim 1, wherein the attachment straps are configured to attach to a leg.

3. The reusable penile attachment of claim 1, wherein the improved penile attachment can be washed and reused.

4. The reusable penile attachment of claim 1, further comprising a pair of boxer shorts, wherein the user is configured to wear the pair of boxer shorts having an interior pocket configured and sized to hold the collection bag.

5. A method to collect urinary leakage of a user comprising the steps of:
a) assembling the cup to the connector and the connector to the tube;

b) putting a lubricant inside the cup or on his penis (or both);
c) pressing on the collection bag so as to remove the air therein and connecting one of the end of the tube to the collection bag;
d) inserting the cup until the exit touches the tip of the glans;
e) gently pulling on the cup so as to create a pressure differential in the area between the exit and the tip of the glans and the ambient pressure outside the cup.

* * * * *